United States Patent [19]
Crainich

[11] Patent Number: 5,645,567
[45] Date of Patent: Jul. 8, 1997

[54] SURGICAL STAPLE AND STAPLER DEVICE THEREFOR

[76] Inventor: Lawrence Crainich, Ceda Road, P.O. box 996, Charlestown, N.H. 03603

[21] Appl. No.: 608,827

[22] Filed: Feb. 29, 1996

Related U.S. Application Data

[62] Division of Ser. No. 281,307, Jul. 27, 1994, Pat. No. 5,544,802.

[51] Int. Cl.$^6$ .................................................. A61B 17/064
[52] U.S. Cl. .................... 606/219; 227/902; 411/472; 411/920; 606/75
[58] Field of Search ........................... 227/19, 85, 88, 227/89, 901, 902; 606/219, 75; 411/471, 472, 473, 920, 457

[56] References Cited

U.S. PATENT DOCUMENTS

| | | | |
|---|---|---|---|
| 4,275,813 | 6/1981 | Noiles | 606/219 X |
| 4,505,273 | 3/1985 | Braun et al. | 606/219 |
| 4,669,647 | 6/1987 | Storace | 227/19 |
| 4,841,960 | 6/1989 | Garner | 606/75 |
| 4,874,122 | 10/1989 | Froelich et al. | 227/19 |
| 4,994,063 | 2/1991 | Garner | 606/75 |
| 5,222,975 | 6/1993 | Crainich | 606/219 |
| 5,413,584 | 5/1995 | Schulze | 606/219 |
| 5,439,468 | 8/1995 | Schulze et al. | 227/901 X |

*Primary Examiner*—Joseph J. Hail, III
*Assistant Examiner*—Jay A. Stelacone
*Attorney, Agent, or Firm*—Bachman & LaPointe, P.C.

[57] ABSTRACT

A surgical staple has a base having first and second base segments defining in an un-deformed state a substantially V-shaped configuration having an apex, each base segment having a first end and a second end. The first end of the first base segment is joined to the first end of the second base segment at the apex of the V-shaped configuration so as to define a first angle between the first base segment and the second base segment of less than about 180° and first and second legs each having a first end and a second end, the first and second legs being connected substantially perpendicularly at the first ends to the second ends of the first and second base segments respectively. A surgical stapler for applying surgical staples according to the invention is also disclosed.

12 Claims, 5 Drawing Sheets

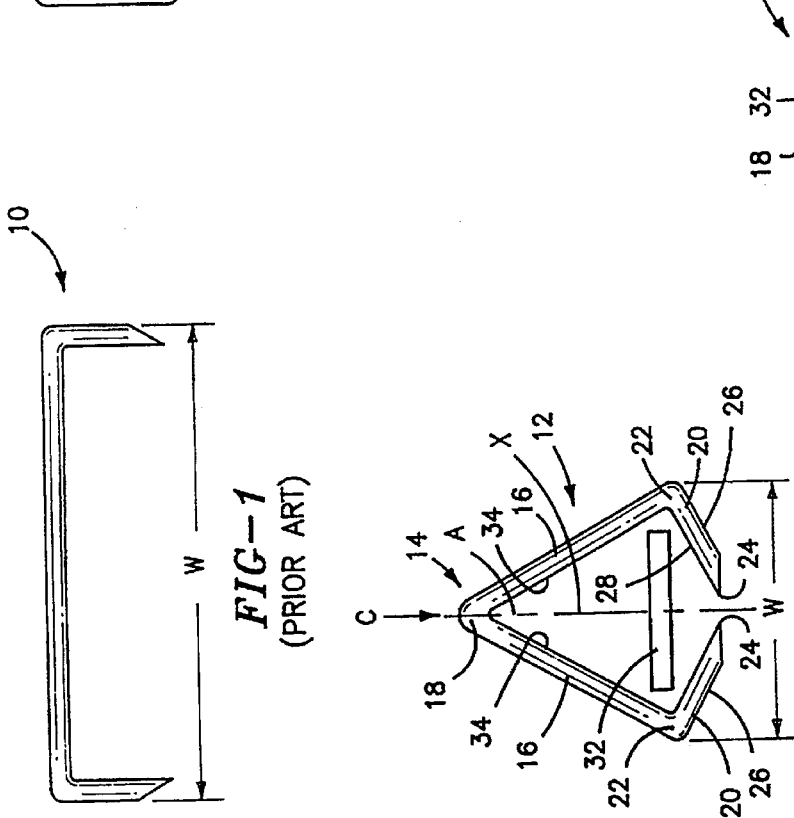

“5,645,567”

SURGICAL STAPLE AND STAPLER DEVICE THEREFOR

This is a Division of application Ser. No. 08/281,307 filed Jul. 27, 1994, now U.S. Pat. No. 5,544,802.

BACKGROUND OF THE INVENTION

The invention relates to a surgical staple having a narrow profile in the un-deformed state, and to a surgical stapler for applying such a staple.

Surgical staples are well known in the art for use in closing incisions or wounds in body tissue, as are surgical stapling apparatus for applying such staples. See for example U.S. Pat. Nos. 4,014,492; 4,043,504; 4,265,226; 4,375,866; 4,399,810; 4,407,286 and 4,607,638.

Conventional surgical staples have a U-shaped configuration with an elongated or broad base portion, relatively square or slightly curved corners and two relatively shorter legs perpendicular to the base and connected thereto at the corners, and terminating at the other end in a sharpened skin or tissue-piercing point. The staples are typically applied by a stapling apparatus wherein a group of same are held in the apparatus and advanced toward an anvil by a staple former having an end with a generally U-shaped recess. The base of the U-shaped recess in the staple former is broader than the anvil, but not as broad as the base of the U-shaped staple. When the staple reaches the anvil, the staple former causes the staple to bend or be deformed around the anvil into an open-sided, substantially O-shaped or rectangular configuration by bending the staple at two points along the elongated base portion. This procedure can be referred to as forming the staple. As this is taking place the sharpened points of the staple enter the tissue on opposite sides of the incision or wound and draw the tissue together. When the staple has been fully formed, the staple former is retracted and the stapler is removed by sliding the anvil out from within the staple or sliding the staple off of the anvil. The staple remains within the tissue to hold the tissue together during healing and is removed after healing by a staple remover. In certain internal applications, staples are used to fasten two tissues together which may not have been severed. Under these circumstances, the staples may be left in place indefinitely if desired.

It is desirable to utilize surgical staples of varying size depending upon the size of the wound or application, and obviously it is desirable to use larger staples for larger wounds or applications. However, conventional U-shaped staples are wide in the un-deformed state and the incision, trocar cannula, etc. through which the staple and stapler are to be conveyed must likewise be wide so as to accommodate the width of the staple. In fact, it can be seen from a consideration of the foregoing that the conventional staple is at its widest prior to deformation, and the stapler must include forming elements sufficiently wide to provide the desired forming of the staple.

It is the primary object of the invention to provide a surgical staple which has a reduced profile or width in the un-deformed state so that the size of the incision or cannula through which the staple must be passed may be reduced.

It is a further object of the invention to provide a stapler for applying surgical staples according to the invention wherein the stapler also has a reduced profile or width.

It is a still further object of the invention to provide such a stapler which is simple and reliable in operation and which exhibits significantly reduced staple jamming.

Other objects and advantages will appear hereinbelow.

SUMMARY OF THE INVENTION

The foregoing objects and advantages are readily attained by the present invention.

In accordance with the invention, surgical staple is provided which comprises a base having a first and second base segments defining in an un-deformed state a substantially V-shaped configuration having an apex, each base segment having a first end and a second end wherein the first end of the first base segment is joined to the first end of the second base segment at the apex of the V-shaped configuration so as to define a first angle between the first base segment and the second base segment of less than about 180°; and first and second legs each having a first end and a second end, the first and second legs being connected substantially perpendicular at the first ends to the second ends of the first and second base segments respectively.

The staple in accordance with the invention has a deformed state wherein the staple has a substantially O-shaped configuration bent at at least one point in each base segment and bent at the apex to a second angle larger than the first angle.

The staple also preferably has an intermediate deformed state wherein only the apex is bent to the second angle.

A surgical stapler for applying staples in accordance with the invention comprises a housing having a diameter; means for storing at least one staple within the housing; forming means within the housing for deforming the staple to a final deformed state wherein the staple has an open sided, substantially O-shaped or rectangular configuration bent at at least one point in each base segment and bent at the apex to a second angle larger than the first angle; and transfer means for transferring a staple from the storing means to the forming means.

The forming means preferably includes a first forming blade for deforming the staple to the intermediate deformed state, and a second forming blade for deforming the staple to the final deformed state.

Elements of the stapler, preferably the anvil and the second forming blade, are preferably laterally deflectable in accordance with the invention so as to provide a narrower profile of the stapler as desired.

BRIEF DESCRIPTION OF THE DRAWINGS

A detailed description of the preferred embodiments of the invention follows, with reference to the attached drawings, wherein:

FIGS. 1 and 2 illustrate the un-deformed and deformed state of conventional surgical staples;

FIGS. 3, 4 and 5 illustrate the un-deformed, intermediate deformed and final deformed state of surgical staples according to the present invention;

DETAILED DESCRIPTION OF THE PREFERRED EMBODIMENT

Figure 6:
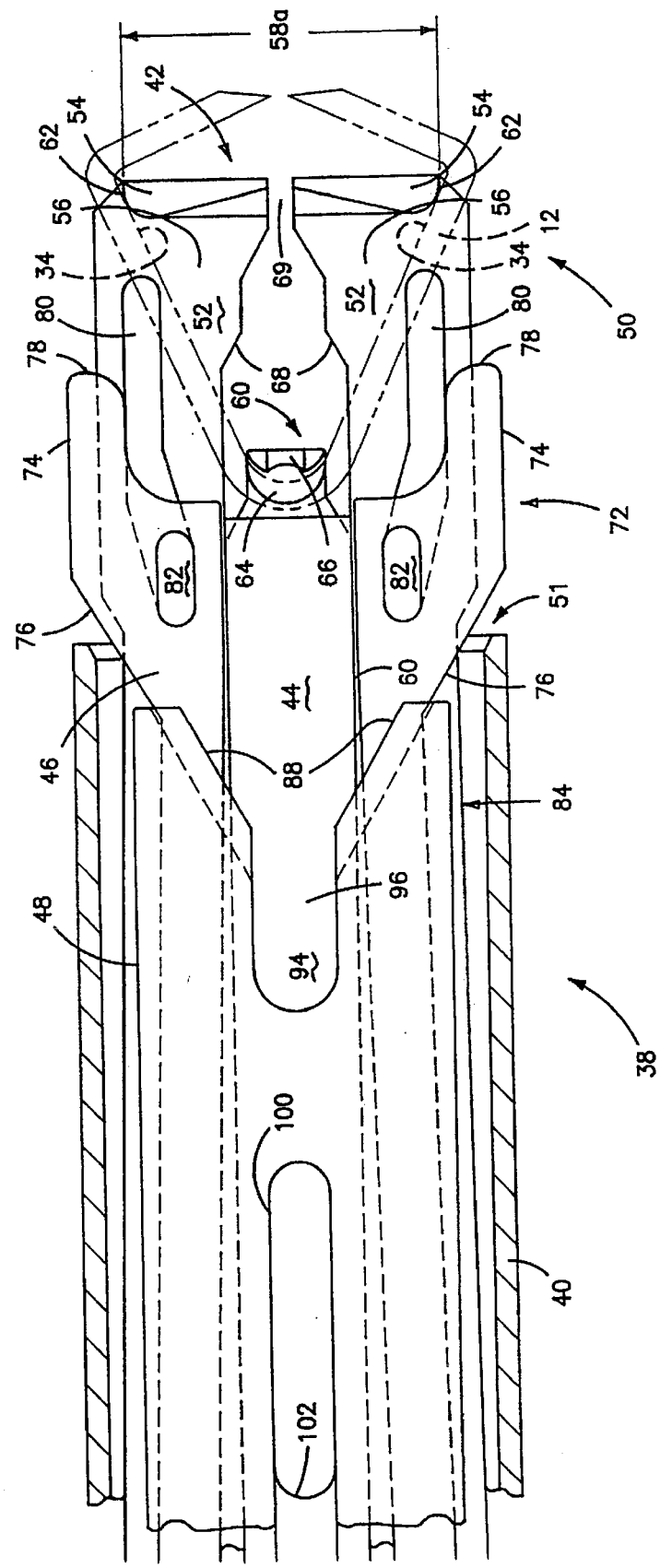
FIG. 6 illustrates a top view of a surgical stapler according to the invention with the various elements in a withdrawn or ready position.

The present invention relates to an improved surgical staple and surgical stapler for use therewith.

As set forth above, surgical staples are widely known and used for holding tissue together during healing and in accordance with numerous other medical procedures. FIGS. 1 and 2 illustrate a conventional surgical staple 10 in an un-deformed state (FIG. 1) and a deformed state (FIG. 2). As illustrated, conventional staples 10 in the un-deformed state have a relatively wide profile. As set forth above, this is undesirable because the staple and even the stapler must frequently be passed through an incision or cannula to reach the tissue in which the staple is to be set and, of course, the incision or cannula must therefore be sufficiently large to accommodate the width of at least the staple in the un-deformed state. It is noted that in laparoscopic surgery it is particularly desirable to have a large staple which is positionable through a small incision or cannula.

FIGS. 3–5 illustrate a surgical staple 12 in accordance with the invention in an un-deformed state (FIG. 3), an intermediate deformed state (FIG. 4), and a final deformed state (FIG. 5). It should be readily apparent that staple 12 in the un-deformed state advantageously has a substantially narrower profile or width W than staple 10 of the prior art (FIG. 1).

FIG. 3 shows staple 12 having a base portion 14 comprising two base segments 16 joined at an apex 18 so as to define a generally V-shaped configuration in the un-deformed state. Legs 20 of staple 12 are joined to base segments 16 at ends 22 of base segments 16 opposite to apex 18. Legs 20 are preferably oriented substantially perpendicular to respective base segments 16 to which they are attached. Legs 20 also preferably have a sharp point 24 at ends opposite to the connection of legs 20 to ends 22 of base segments 16. An interior angle A is defined between base segments 16 around apex 18. In accordance with the invention, angle A in the un-deformed state is preferably less than 180°, more preferably less than or equal to about 90°, and ideally approximately 50° so that width W of staple 12 is significantly smaller than conventional staples 10 in the un-deformed state. In the un-deformed state, legs 20 are pointed generally toward each other as shown in FIG. 3 and preferably extend toward each other along intersecting courses. Points 24 are preferably in close proximity to one another, also as shown in FIG. 3.

Points 24 may be formed on legs 20 in any desired manner. However, it is preferable that point 24 be formed by a sloping surface tapering inward from an outer edge 26 of leg 20 toward an inner edge 28 thereof. In this way, points 24, when deployed into tissue, will easily penetrate same because of the arc followed by the points 24 of legs 20 of the staple upon insertion.

Staple 12 in accordance with the invention has an intermediate deformed state or position (FIG. 4), and a final deformed state (FIG. 5). Staple 12 in use is deformed to the intermediate deformed state and the final deformed state in a series of steps which may be substantially simultaneous but which are preferably carried out sequentially so as to first open staple 12 to the intermediate deformed state of FIG. 4, and then to bend each of base segments 16 into the final deformed state of FIG. 5.

In the intermediate deformed state, base segments 16 are bent to a wider interior angle B defined around apex 18. Angle B is preferably bent in the intermediate deformed state to an angle larger than angle A and preferably angle B is about 180° so as to define, in the intermediate deformed state, a substantially U-shaped configuration.

In the final deformed state, each base segment 16 is bent or deformed at at least one point 30 so as to provide the desired open-sided and substantially O-shaped or rectangular configuration of the final deformed state of FIG. 5.

In accordance with the invention, staple 12 may advantageously be positioned through an incision or cannula to an area of use in the narrow profile un-deformed state of FIG. 3. Sequential deforming at this point is preferable so that staple 12 may be bent to the intermediate deformed state for additional fine adjustment of position relative to the subject body tissue prior to final deformation or bending into the final deformed state of FIG. 5.

As set forth above, the maximum width W of staple 12, measured laterally to the axis of symmetry X of staple 12, is smallest in the un-deformed state, thereby allowing use of staple 12 with a smaller incision or cannula as desired.

In accordance with the invention, staple 12 may be deformed, preferably sequentially as desired, around an anvil 32 schematically illustrated in FIGS. 3–5.

Staple 12 is initially positioned with inner sides 34 in proximity with anvil 32 substantially as shown. Application of a force, preferably in the vicinity of apex 18 and toward anvil 32 as illustrated by arrow C serves to bend or deform staple 12, at apex 18, to the intermediate deformed state of FIG. 4.

At this point, further application of force to staple 12, preferably to base segments 16 at points 36 where they extend beyond anvil 32 as illustrated by arrows D, serves to bend each segment 16 at point 30 to provide the final deformed state of FIG. 5.

It should be readily apparent that the staple according to the invention in the final deformed state (FIG. 5) is substantially similar to conventional staples in the deformed state (FIG. 2). A hump at apex 18 may result without detriment. (See FIG. 5). However, staples according to the invention advantageously have a narrower profile (FIG. 3) in the un-deformed state than conventional un-deformed staples (FIG. 1). This allows surgeons to use staples which have the same final size and, thus, closure ability, while requiring incisions or cannulas of a desirable smaller size.

In further accordance with the invention, a stapler is provided for use in applying surgical staples 12 according to the invention.

Figure 11:
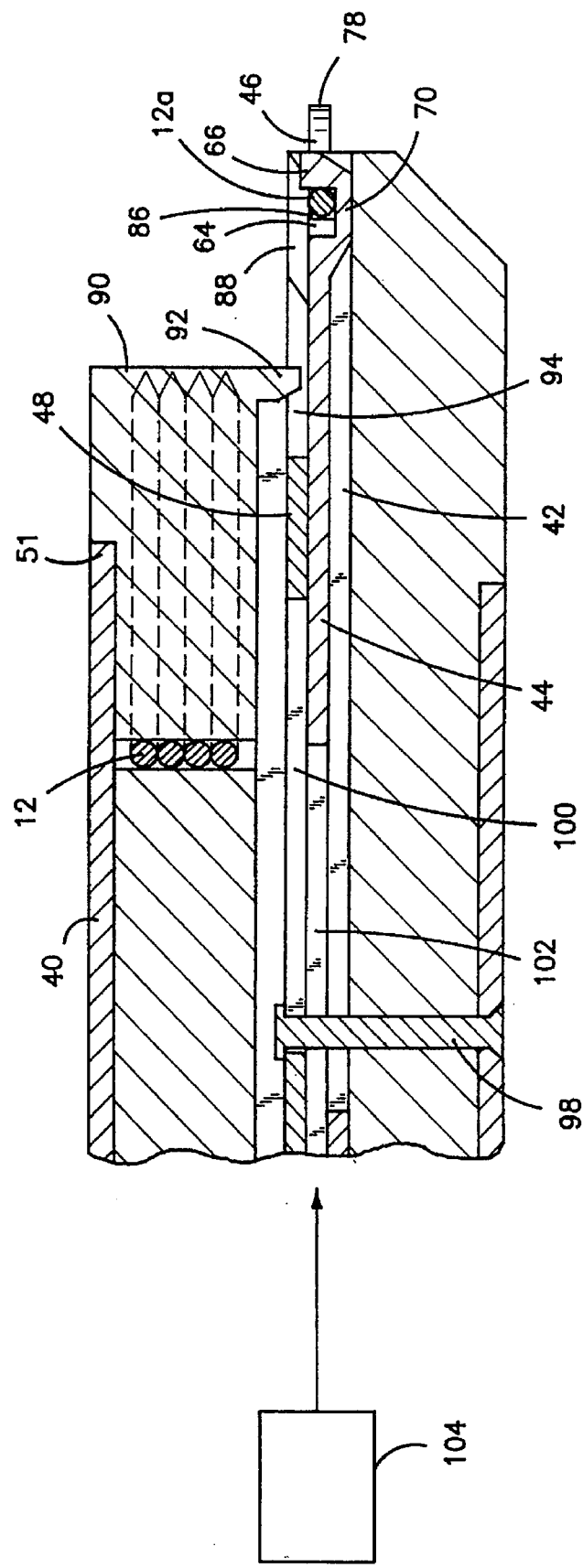
FIG. 11 is a cross-section taken along a center line of a stapler according to the invention and shows a plurality of staples stacked in a cartridge.

FIG. 6 illustrates a top partially sectional view of a surgical stapler 38 according to the invention (See also FIG. 11). Stapler 38 preferably includes a housing 40, anvil 42, first forming blade 44, second forming blade 46, and positioning blade 48, as well as a storage magazine and a trigger mechanism (not shown in FIG. 6).

In accordance with the invention, housing 40 may preferably comprise a substantially elongated tubular member which houses the various elements of stapler 38. Of course, housing 40 may suitably be of other shape or configuration and the exact shape of housing 40 is not critical.

Anvil 42 (See also FIG. 8) preferably comprises a substantially flat member with formed up ends mounted within housing 40 and preferably having an extending portion 50 protruding from an end 51 of housing 40. Extending portion 50 preferably has a substantially flat surface 52 on which a staple 12 is positioned prior to application or firing, and an upwardly projecting anvil surface 54 around and against which staple 12 is deformed during application. Anvil 42 is preferably fixed longitudinally relative to housing 40. Anvil 42 also preferably has two anvil elements 56 each carrying a portion of anvil surface 54 and being laterally deflectable relative to each other so that the width 58 of anvil surface 54 is adjustable between wide and narrow positions 58b (FIG. 7) 58a (FIG. 6), respectively. This is achieved positively when first forming blade 44 cams open the anvil elements 56. The spring temper of the material of which anvil 42 is made serves to retract the anvil laterally when blade 44 is withdrawn.

The adjustable width is desirable in accordance with the invention as anvil surface 54 may be withdrawn to the narrow width when staples 12 are not being formed thereon. In this way, in accordance with the overall objective of the invention, stapler 38 has a narrower diametrical profile or width and therefore can be utilized with a smaller incision or cannula.

Figure 9:
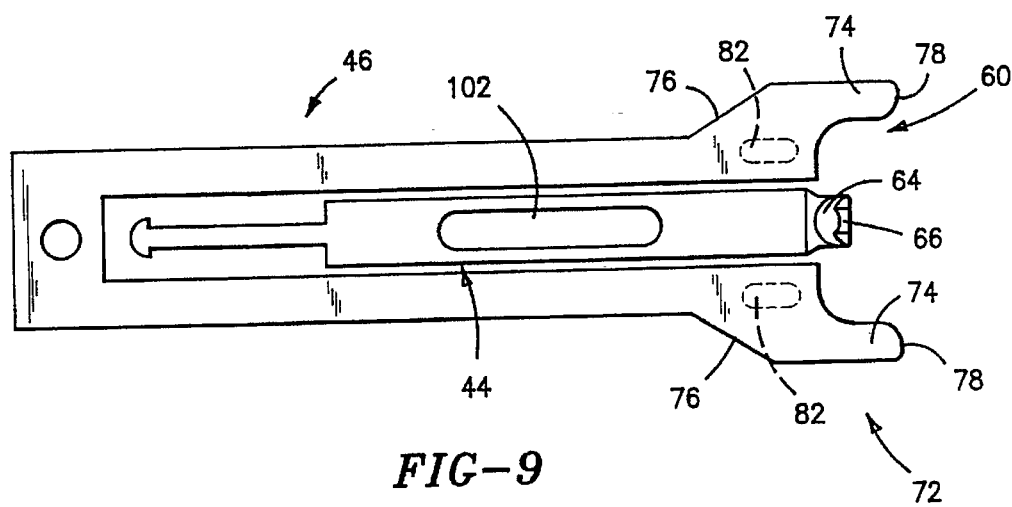
FIG. 9 is a top view of forming blade elements in accordance with the invention.

First forming blade 44 (See also FIG. 9) preferably comprises a substantially flat member slidably mounted within housing 40 and having an operative end 60 arranged in the vicinity of extending portion 50 of anvil 42. Preferably, blade 44 is arranged above anvil elements 56 and has at least a portion which extends downwardly between elements 56. Blade 44 is operative to push a staple 12 in position on surface 52 (shown in dashed lines in FIG. 6) against anvil surface 54 so that inner sides 34 of staple 12 contact sides 62 of anvil surface 54 and are deflected thereby so as to bend staple 12, preferably substantially at apex 18, to the wider angle B, preferably about 180°, as discussed above and schematically illustrated in FIG. 4. Operative end 60 when displaced toward anvil surface 54 serves to apply the force represented in FIG. 3 by arrow C.

Operative end 60 of blade 44 preferably has a notch 64 for receiving a portion of staple 12 when staple 12 is delivered by positioning blade 48, the operation of which is fully described below.

Figure 7:
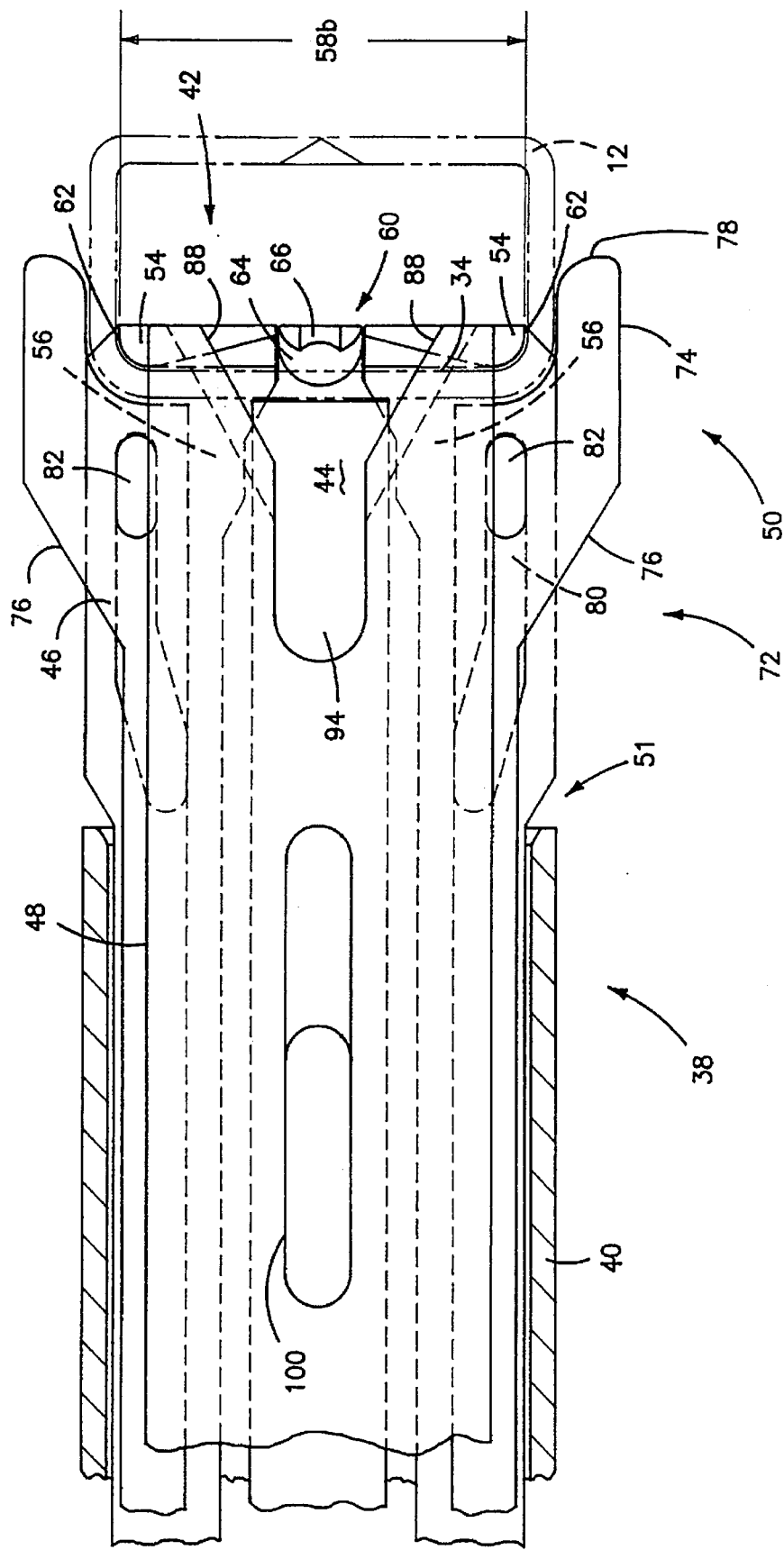
FIG. 7 illustrates a similar view to FIG. 6, with the elements in an extended or fired position.
Figure 8:
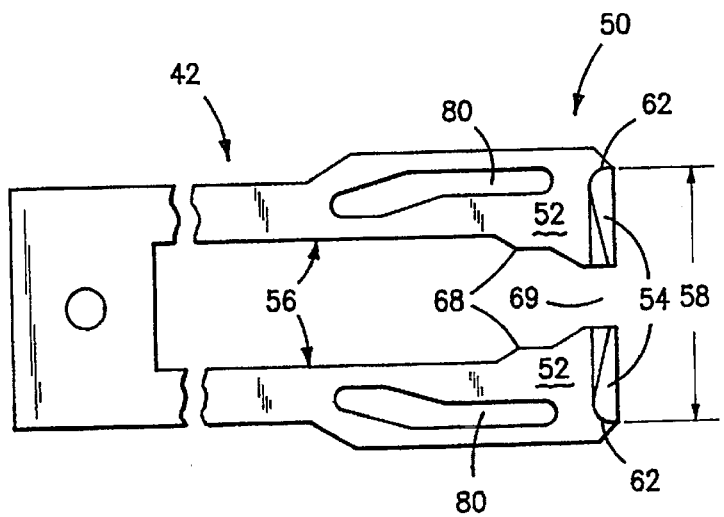
FIG. 8 is a top view of an anvil element according to the invention.

Notch 64 may preferably be defined by a nose portion 66 formed or attached to operative end 60. Blade 44 is preferably centrally located as shown, and slidable in housing 40 between a withdrawn position as shown in FIG. 6 and an extended position as shown in FIG. 7. In the withdrawn position, notch 64 is preferably arranged so as to receive apex 18 of staple 12 so that staple 12 is firmly engaged by blade 44. In the extended position of FIG. 7, anvil 42 and forming blade 46 also extend laterally in accordance with the invention so as to form a staple having a wide final deformed state as will be further described below.

It is noted that inner edges 68 of anvil elements 56 may preferably be gradually tapered inwardly toward each other with a gap 69 therebetween as shown, and operative end 60 may have a downwardly extending portion 70 (shown in FIG. 11) extending into the plane of anvil elements 56 of anvil 42 at gap 69. In this configuration, when blade 44 is displaced toward anvil surface 54, downwardly extending portion 70 of operative end 60 contacts inner edges 68 of anvil elements 56 and deflects elements 56 to the wide position for forming of staple 12, all as desired.

Second forming blade 46 (See also FIG. 9) preferably also comprises a substantially flat member slidably disposed within housing 40. Blade 46 is also slidable between a withdrawn position as shown in FIG. 6 and an extending position as shown in FIG. 7. Blade 46 preferably has an operative end 72 operative to form staple 12 around anvil surface 54 so as to deform staple 12 from the intermediate state of FIG. 4 to the final deformed state of FIG. 5. Operative end 72 preferably includes two forming arms 74 arranged relative to anvil surface 54 so that displacement of blade 46 to the extending position displaces forming arms 74 beyond anvil surface 54 and to either side thereof as shown in FIG. 7. Arms 74 are preferably also laterally deflectable between a wide and a narrow position. The narrow position corresponds to the withdrawn position of FIG. 6 in further accord with the overall objective of the invention to provide a staple/stapler having a narrow profile. In this regard, arms 74 preferably have a rearwardly tapered exterior edge 76 arranged relative to housing 40 so that displacement of blade 46 into the withdrawn position urges exterior edges 76 against housing 40 and thereby deflects arms 74 into the narrow position as desired.

Forward edges 78 of arms 74 may suitably be rounded so as to facilitate smooth operation of stapler 38 during contact of edges 78 with staple 12 and to thereby reduce the likelihood of staple jamming and promote smooth forming. In this regard, forward edges 78 serve to apply the force represented in FIG. 4 by arrows D.

In further accordance with the invention, guides may be provided to guide arms 74 to the proper deflected position relative to anvil surface 54. As shown in FIGS. 6–7, such guides may include tracks 80 or grooves formed for example in surface 52 of anvil 42 and projections 82 mounted to arms 74 and extending into tracks 80. When arms 74 are displaced into the extending position, tracks 80 and projections 82 cooperate to laterally guide or deflect arms 74 around anvil surface 54 and into the wide position. Of course, numerous other structural configurations could suitably be used for guiding arms 74 as desired. For example, similar tracks could be located on arms 74, with projections on surface 52.

In accordance with the foregoing, it should be noted that, advantageously, arms 74 and anvil 42 have a width less than or equal to the diameter of housing 40 when in the withdrawn position of FIG. 6. When extended so as to deform and apply a staple 12, however, the width of both anvil 42 and arms 74 passing to either side thereof are expanded to an increased spacing or width so as to provide the desired width of staple 12 in the final deformed state.

Figure 10:
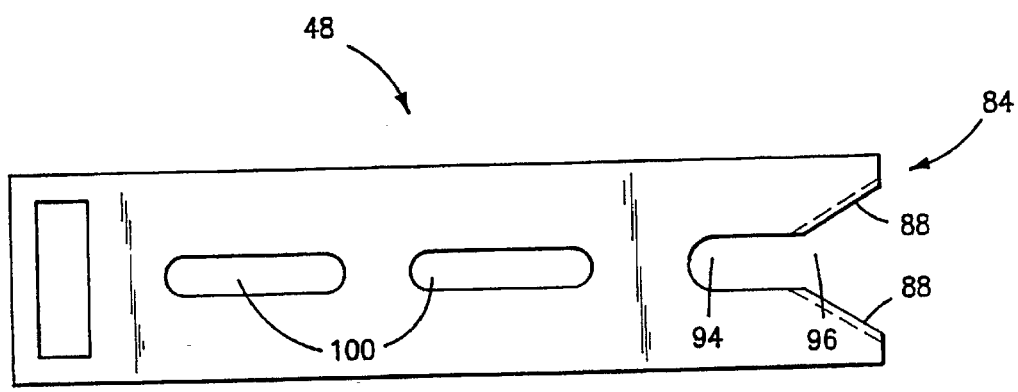
FIG. 10 is a top view of a positioning blade element according to the invention.

Positioning blade 48 (See also FIG. 10) preferably also comprises a substantially flat member slidably mounted within housing 40 so as to deliver staples 12 from a staple magazine (described below) to a ready or cocked position on surface 52 between anvil surface 54 and first forming blade 44, with apex 18 of staple 12 firmly seated in notch 64 of first forming blade 44.

Positioning blade 48 preferably has an operative end 84 having an open V-shaped configuration for receiving the outside contour of a staple 12. Blade 48 is slidable in housing 40 between a withdrawn position (FIG. 6) and an extended position (FIG. 7). In the withdrawn position, blade 48 is positioned so as to receive a staple 12 from a staple supply. As positioning blade 48 is displaced toward the extended position, staple 12 is forwardly displaced as well, until apex 18 of staple 12 reaches notch 64 of underlying first forming blade 44. At this point, staple 12 drops into notch 64 and further extending displacement of positioning blade 48 causes operative end 84 of blade 48 to pass over staple 12 to the fully extended position of FIG. 7 wherein positioning blade 48 and surface 52 of anvil 42 define a gap 86 therebetween in which staple 12a (See FIG. 11) is snugly held so as to prevent jamming or escape or other undesirable improper orientation of staple 12 during deformation. In this regard, positioning blade 48 may preferably be slidably mounted directly on top of first and second forming blade 44,46 as shown in FIG. 11. Further, anvil surface 54 is preferably provided having a height selected so that leading edges 88 of operative end 84 of positioning blade 48 extend just over, and are preferably in substantially close proximity or in contact with anvil surface 54 in the extended position as best shown in FIG. 7.

Leading edges 88 of positioning blade 48 also preferably have a profile which tapers upwardly toward the forwarded end of blade 48. This tapered profile may preferably extend along substantially the entire surface of the open V-shaped configuration of operative end 84. The taper serves, advantageously, to apply a downwardly directed force to staple 12 so as to ensure the desired dropping of staple 12 into notch 64 of first forming blade 44 and onto surface 52 of anvil 42. Such a taper also helps to ensure clean removal of a staple 12 from the staple storage or supply member, thereby further preventing jamming of the stapler.

Referring now to FIG. 11, it is noted that staples 12 are preferably supplied one at a time to positioning blade 48, preferably along a course substantially perpendicular to the direction of sliding of positioning blade 48. As shown in FIG. 11, a storage member 90 may suitably be provided within housing 40 holding a downwardly biased stack of staples 12. In this configuration, a staple 12 is downwardly pushed into position within the open V-shaped configuration of positioning blade 48. When blade 48 is extended as shown in FIG. 11, staple 12 is positioned at anvil 42 and subsequently formed around anvil 42 by blades 44, 46. When positioning blade 48 is again withdrawn, the next staple 12 drops into position within the open V-shaped configuration of positioning blade 48 for positioning and forming as desired. Storage member 90 may also preferably have a downwardly oriented projection 92 arranged substantially in alignment with nose 66 of blade 44 in the withdrawn position. Projection 92 preferably extends or projects into the path of displacement of staple 12 when staple 12 is conveyed from storage member 90 by positioning blade 48. Projection 92 serves to further urge apex 18 of staple 12 into notch 64 of first forming blade 44. Further, positioning blade 48 preferably has a groove extension 94 extending backwardly or rearwardly from base or apex 96 of the V-shaped configuration thereof. Groove extension 94 serves to receive projection 92 of storage member 90 so that positioning blade 48 may be freely extended to the fully extended position without obstruction by projection 92 as shown in FIG. 11.

FIG. 11 also further illustrates a suitable method for slidably mounting positioning blade 48 and first and second forming blades 44,46. As shown, housing 40 may have upwardly extending lugs 98, and positioning blade 48 may suitably be provided with a groove 100, lugs 98 extending through groove 100 to provide longitudinal sliding of positioning blade 48 as desired. First forming blade 44 may also be provided with a groove 102 for slidable mounting on lugs 98. Second forming blade 46 may suitably be disposed between positioning blade 48 and longitudinally fixed anvil 42 disposed thereunder so as to be slidably "sandwiched" within housing 40. Of course, numerous other configurations are available and suitable for such slidable mounting.

A trigger member 104 (schematically illustrated in FIG. 11) is also provided for operating the elements of stapler 38 to provide the desired deformation of staples 12. In this regard, trigger member 104 is preferably operable to selectively and/or sequentially operate positioning blade 48, first forming blade 44, and second forming blade 46, preferably in that order. Numerous trigger assemblies are known in the art for providing such operation, any of which may suitably be utilized in accordance with the invention. The sequential extension of positioning blade 48, first forming blade 44 and second forming blade 46 is desirable so that staples 12 may sequentially be (1) positioned by blade 48, (2) bent to the intermediate deformed state (FIG. 4) by blade 44, and (3) then bent to the final deformed state (FIG. 5) by blade 46.

Trigger member 104 is also preferably operative to withdraw blades 44,46,48 after placement of a staple so as to ready stapler 38 for the next staple. Withdrawal need not be sequentially performed, however, and may be carried out in any convenient order or simultaneously if desired.

In accordance with the foregoing, a surgical staple and a stapler for applying the staple have been provided which allow application of the staple through a narrower incision or smaller diameter cannula than was possible with conventional staples. Further, the stapler device is efficient, reliable, easy to use, and highly resistant to jamming.

It is apparent that there has been provided in accordance with this invention a surgical staple and stapler device therefor which fully satisfies the objects, means, and advantages set forth hereinbefore. While the invention has been described in combination with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A surgical staple, comprising:

a base having first and second base segments defining in an un-deformed state a substantially V-shaped configuration having an apex, each base segment having a first end and a second end wherein the first end of the first base segment is joined to the first end of the second base segment at the apex of the V-shaped configuration as so to define a first interior angle between the first base segment and the second base segment of less than about 180°; and first and second substantially straight legs each having a first end and a second end terminating, wherein each second end terminates in a point, the first and second legs being connected at the first ends to the second ends of the first and second base segments respectively; and wherein the points of the first and second legs extend generally toward each other from the second ends of first and second base segments on converging paths.

2. A surgical staple according to claim 1, wherein the staple in a deformed state has a substantially configuration bent at at least one point in each base segment and bent at the apex to a second interior angle larger than the first interior angle.

3. A surgical staple according to claim 2, wherein the first interior angle is less than or equal to about 90°.

4. A surgical staple according to claim 3, wherein the second interior angle is about 180°.

5. A surgical staple according to claim 2, wherein the staple in an intermediate deformed state is bent at the apex to the second interior angle.

6. A surgical staple according to claim 5, wherein the staple has an axis of symmetry drawn through the apex and dividing the first base segment and the first leg from the second base segment and the second leg, wherein the staple has a maximum width measured lateral to the axis of symmetry, and wherein the maximum width of the staple in the un-deformed state is narrower than the maximum width of the staple in the intermediate deformed state and narrower than the maximum width of the staple in the deformed state.

7. A surgical staple according to claim 2, wherein the staple has an axis of symmetry drawn through the apex and dividing the first base segment and the first leg from the second base segment and the second leg, wherein the staple has a maximum width measured lateral to the axis of symmetry, and wherein the maximum width of the staple in the un-deformed state is narrower than the maximum width of the staple in the deformed state.

8. A surgical staple according to claim 1, wherein the first interior angle is less than or equal to about 90°.

9. A surgical staple according to claim 1, wherein the first and second base segments and the first and second legs are substantially planar in configuration.

10. A surgical staple, comprising:

a base having first and second base segments defining in an un-deformed state a substantially V-shaped configuration having an apex, each base segment having a first end and a second end wherein the first end of the first base segment is Joined to the first end of the second base segment at the apex of the V-shaped configuration as so to define a first interior angle between the first base segment and the second base segment of less than about 180°; and first and second legs each having a first end and a second end, the first and second legs being connected substantially perpendicular at the first ends to the second ends of the first and second base segments respectively, wherein the staple in a final deformed state has a substantially rectangular configuration bent at at least one point in each base segment and bent at the apex to a second interior angle larger than the first interior angle, and wherein the first and second interior angles are defined with respect to edges of the base segments that are directed inwardly of the substantially rectangular configuration when the staple is in the final deformed state.

11. A surgical staple according to claim 10, wherein the second ends of the first and second legs each terminate in a sharp point.

12. A surgical staple according to claim 11, wherein the points of the first and second legs extend generally toward each other from the second ends of the first and second base segments on converging paths.

* * * * *

UNITED STATES PATENT AND TRADEMARK OFFICE
CERTIFICATE OF CORRECTION

PATENT NO. : 5,645,567
DATED : July 8, 1997
INVENTOR(S) : Lawrence Crainich It is certified that error appears in the above-identified patent and that said Letters Patent is hereby corrected as shown below:

IN COLUMN 8, CLAIM 1, LINE 38, AFTER "END" (SECOND OCCURRENCE) DELETE "TERMINATING".

IN COLUMN, 9, CLAIM 10, line 17 "Joined" should read--joined--.

Signed and Sealed this

First Day of December, 1998

Attest:

BRUCE LEHMAN

Attesting Officer

Commissioner of Patents and Trademarks